United States Patent
Taimisto

(10) Patent No.: US 6,923,808 B2
(45) Date of Patent: Aug. 2, 2005

(54) PROBES HAVING HELICAL AND LOOP SHAPED INFLATABLE THERAPEUTIC ELEMENTS

(75) Inventor: Miriam H. Taimisto, San Jose, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 5 days.

(21) Appl. No.: 10/373,451

(22) Filed: Feb. 24, 2003

(65) Prior Publication Data

US 2004/0167509 A1 Aug. 26, 2004

(51) Int. Cl.[7] .................................................. A61B 18/14
(52) U.S. Cl. ................................................................. 606/41
(58) Field of Search ............................. 606/41; 607/99, 607/122

(56) References Cited

U.S. PATENT DOCUMENTS

| | | |
|---|---|---|
| 4,419,094 A | 12/1983 | Patel |
| 4,706,671 A | 11/1987 | Weinrib |
| 4,834,724 A | 5/1989 | Geiss |
| 4,976,711 A | 12/1990 | Parins |
| 5,016,808 A | 5/1991 | Heil, Jr. |
| 5,054,501 A | 10/1991 | Chuttani |
| 5,057,106 A | 10/1991 | Kasevich et al. |
| 5,163,431 A | 11/1992 | Griep |
| 5,228,442 A | 7/1993 | Imran |
| 5,239,999 A | 8/1993 | Imran |
| 5,279,299 A | 1/1994 | Imran |
| 5,411,546 A | 5/1995 | Bowald |
| 5,549,661 A | 8/1996 | Kordis |
| 5,582,609 A | 12/1996 | Swanson |
| 5,716,410 A | 2/1998 | Wang |
| 5,800,482 A | 9/1998 | Pomeranz |
| 5,836,925 A | 11/1998 | Soltesz |
| 5,836,947 A | 11/1998 | Fleischman |
| 5,860,974 A | 1/1999 | Abele |
| 5,895,417 A | 4/1999 | Pomeranz |
| 5,938,694 A | 8/1999 | Jaraczewski |
| 5,971,983 A | 10/1999 | Lesh |
| 5,972,019 A | 10/1999 | Engelson |
| 6,012,457 A | 1/2000 | Lesh |
| 6,016,809 A | 1/2000 | Mulier |
| 6,024,740 A | 2/2000 | Lesh |
| 6,048,329 A | 4/2000 | Thompson |
| 6,071,274 A | 6/2000 | Thompson |
| 6,071,279 A | 6/2000 | Whayne |
| 6,071,281 A | 6/2000 | Burnside |
| 6,076,012 A | 6/2000 | Swanson |
| 6,106,522 A | 8/2000 | Fleischman |
| 6,117,101 A | 9/2000 | Diederich |
| 6,152,920 A | 11/2000 | Thompson |
| 6,203,525 B1 | 3/2001 | Whayne |
| 6,280,441 B1 | 8/2001 | Ryan |
| 6,290,697 B1 | 9/2001 | Tu |
| 6,325,797 B1 | 12/2001 | Stewart |
| 6,371,928 B1 | 4/2002 | Mcfann |
| 6,391,018 B1 | 5/2002 | Tanaka |
| 6,464,700 B1 | 10/2002 | Koblish |
| 6,468,272 B1 | 10/2002 | Koblish |
| 6,529,756 B1 | 3/2003 | Phan |

(Continued)

FOREIGN PATENT DOCUMENTS

| | | |
|---|---|---|
| EP | 1042990 A1 | 10/2000 |
| WO | WO 99/02096 A1 | 1/1999 |
| WO | WO 99/34741 A1 | 7/1999 |
| WO | WO 00/01313 A1 | 1/2000 |
| WO | WO 01/37723 A2 | 5/2001 |
| WO | WO 01/37746 A1 | 5/2001 |
| WO | WO 01/72234 A1 | 10/2001 |
| WO | WO 02/17804 A2 | 3/2002 |

*Primary Examiner*—Lee S. Cohen
(74) *Attorney, Agent, or Firm*—Henricks, Slavin & Holmes LLP

(57) ABSTRACT

A probe that facilitates the creation of circumferential lesions in body tissue. The probe includes a probe body and an inflatable helical or loop shaped therapeutic element.

34 Claims, 4 Drawing Sheets

U.S. PATENT DOCUMENTS

| | | |
|---|---|---|
| 6,542,781 B1 | 4/2003 | Koblish |
| 6,579,288 B1 | 6/2003 | Swanson |
| 6,711,444 B2 | 3/2004 | Koblish |
| 6,745,080 B2 | 6/2004 | Koblish |
| 2001/0007070 A1 | 7/2001 | Stewart |
| 2001/0007071 A1 | 7/2001 | Koblish |
| 2001/0020174 A1 | 9/2001 | Koblish |
| 2002/0004644 A1 | 1/2002 | Koblish |
| 2002/0026187 A1 | 2/2002 | Swanson |
| 2002/0068897 A1 | 6/2002 | Jenkins |
| 2003/0069570 A1 * | 4/2003 | Witzel et al. .................. 606/28 |

* cited by examiner

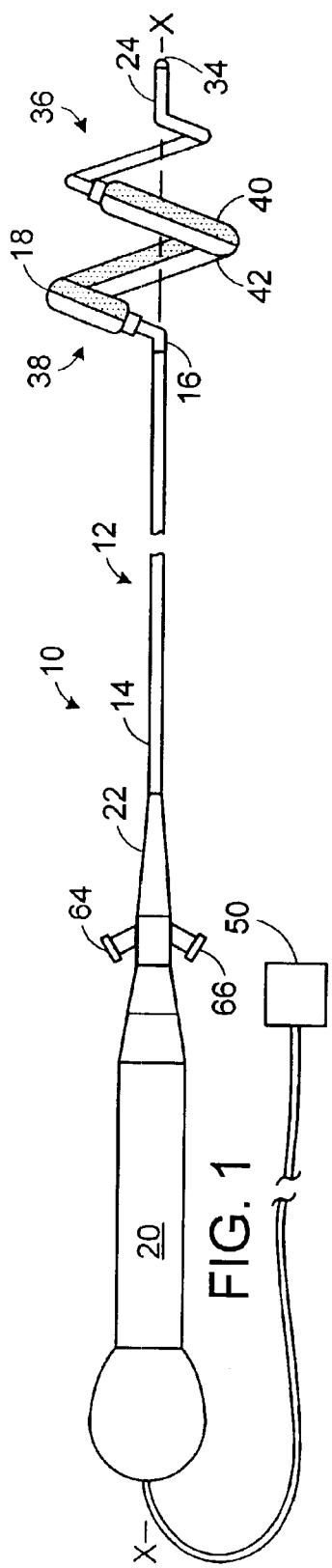
FIG. 1
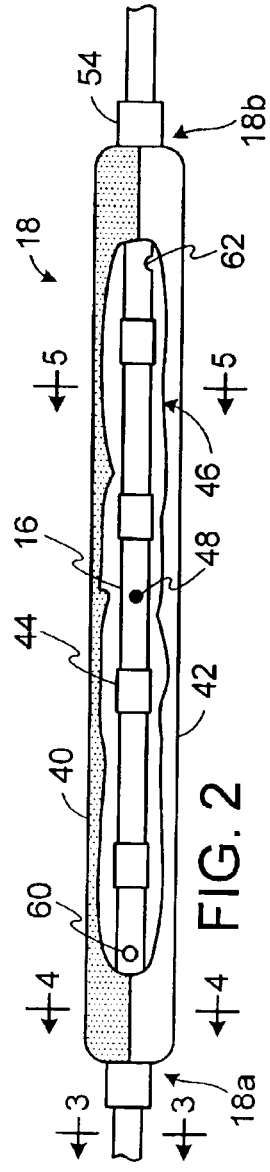
FIG. 2
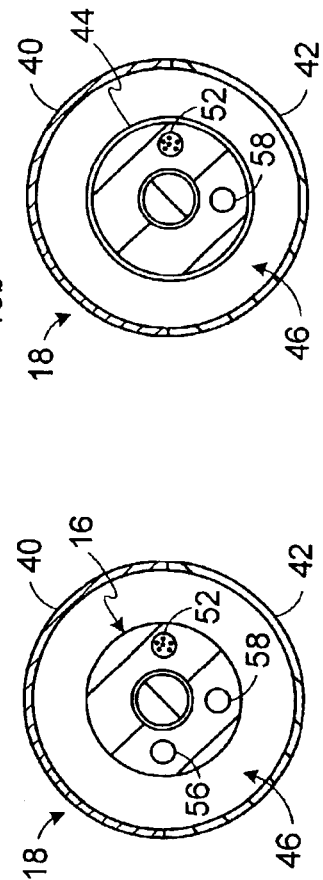
FIG. 4
FIG. 5
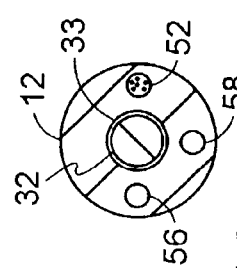
FIG. 3

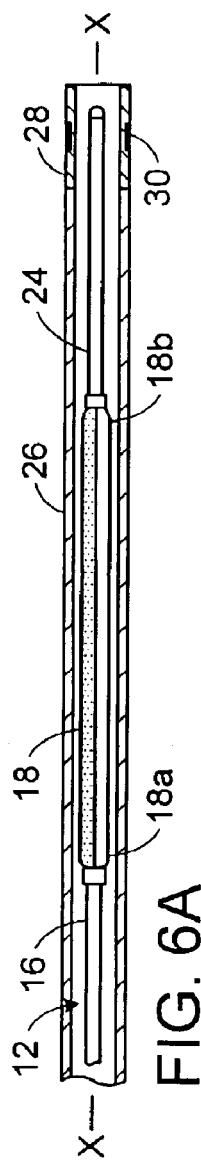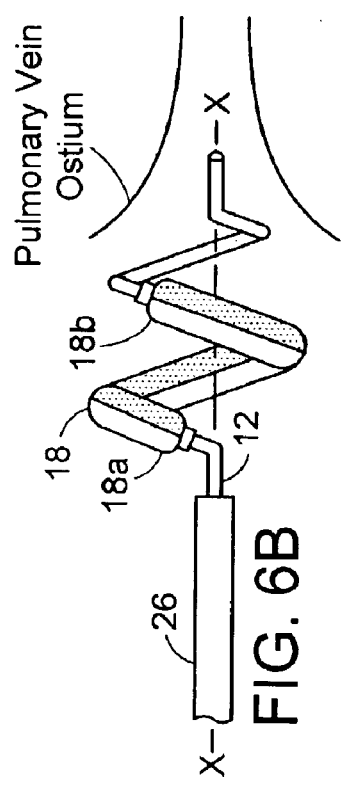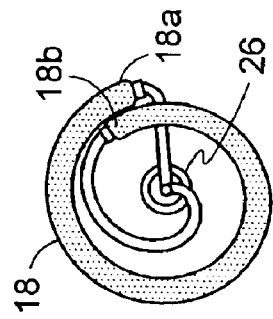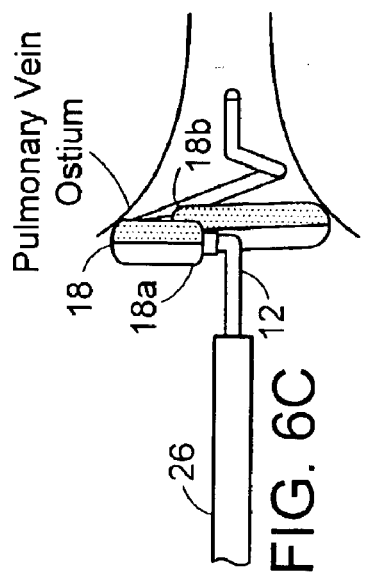

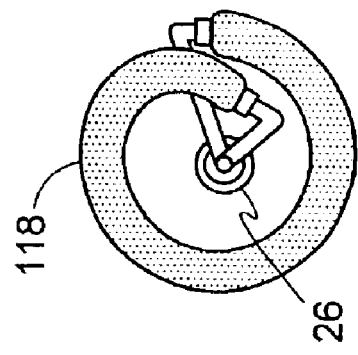
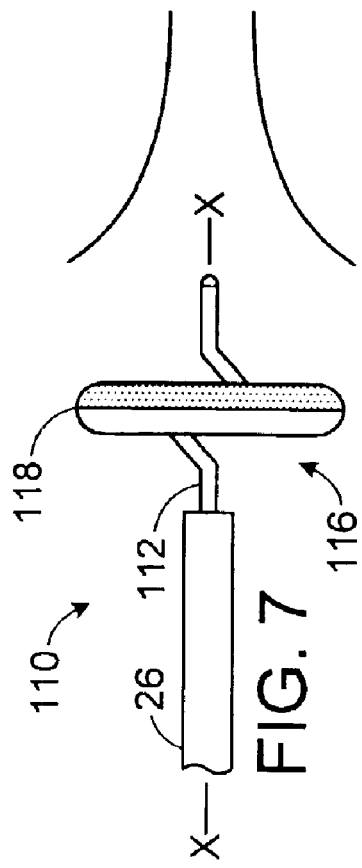
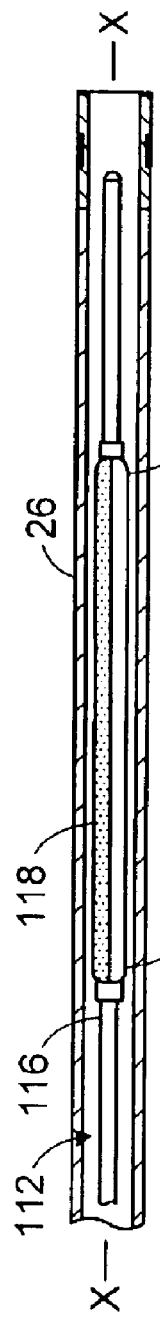

PROBES HAVING HELICAL AND LOOP SHAPED INFLATABLE THERAPEUTIC ELEMENTS

BACKGROUND OF THE INVENTIONS

1. Field of Inventions

The present inventions relate generally to medical devices that support therapeutic elements in contact with body tissue.

2. Description of the Related Art

There are many instances where therapeutic elements must be inserted into the body. One instance involves the treatment of cardiac conditions such as atrial fibrillation and atrial flutter which lead to an unpleasant, irregular heart beat, called arrhythmia.

Normal sinus rhythm of the heart begins with the sinoatrial node (or "SA node") generating an electrical impulse. The impulse usually propagates uniformly across the right and left atria and the atrial septum to the atrioventricular node (or "AV node"). This propagation causes the atria to contract in an organized way to transport blood from the atria to the ventricles, and to provide timed stimulation of the ventricles. The AV node regulates the propagation delay to the atrioventricular bundle (or "HIS" bundle). This coordination of the electrical activity of the heart causes atrial systole during ventricular diastole. This, in turn, improves the mechanical function of the heart. Atrial fibrillation occurs when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria. Because of a loss of atrioventricular synchrony, the people who suffer from atrial fibrillation and flutter also suffer the consequences of impaired hemodynamics and loss of cardiac efficiency. They are also at greater risk of stroke and other thromboembolic complications because of loss of effective contraction and atrial stasis.

One surgical method of treating atrial fibrillation by interrupting pathways for reentry circuits is the so-called "maze procedure" which relies on a prescribed pattern of incisions to anatomically create a convoluted path, or maze, for electrical propagation within the left and right atria. The maze procedure has been found very effective in curing atrial fibrillation. However, the maze procedure is technically difficult to do. It also requires open heart surgery and is very expensive. Maze-like procedures have also been developed utilizing catheters which can form lesions on the endocardium (the lesions being 1 to 15 cm in length and of varying shape) to effectively create a maze for electrical conduction in a predetermined path. The formation of these lesions by soft tissue coagulation (also referred to as "ablation") can provide the same therapeutic benefits that the complex incision patterns that the surgical maze procedure presently provides, but without invasive, open heart surgery.

Catheters used to create lesions typically include a relatively long and relatively flexible body portion that has a soft tissue coagulation electrode on its distal end and/or a series of spaced tissue coagulation electrodes near the distal end. The portion of the catheter body portion that is inserted into the patient is typically from 23 to 55 inches in length, with another 8 to 15 inches, including a handle, outside the patient. The length and flexibility of the catheter body allow the catheter to be inserted into a main vein or artery (typically the femoral vein), directed into the interior of the heart, and then manipulated such that the coagulation electrode contacts the tissue that is to be ablated. Fluoroscopic imaging is used to provide the physician with a visual indication of the location of the catheter.

In some instances, the proximal end of the catheter body is connected to a handle that includes steering controls. Exemplary catheters of this type are disclosed in U.S. Pat. No. 5,582,609. In other instances, the catheter body is inserted into the patient through a sheath and the distal portion of the catheter is bent into a loop that extends outwardly from the sheath. This may be accomplished by pivotably securing the distal end of the catheter to the distal end of the sheath, as is illustrated in U.S. Pat. No. 6,071,279. The loop is formed as the catheter is pushed in the distal direction. The loop may also be formed by securing a pull wire to the distal end of the catheter that extends back through the sheath, as is illustrated in U.S. Pat. No. 6,048,329. One lesion that has proved difficult to form with conventional steerable and loop devices was the circumferential lesion that is formed within the pulmonary vein, or in the tissue surrounding the pulmonary vein, which isolates the pulmonary vein and cures ectopic atrial fibrillation.

More recently, catheters with inflatable energy emitting elements that are capable of forming circumferential therapeutic lesions have been proposed. Such energy emitting elements are solid, generally spherical, balloon-like structures that, when inflated, have a diameter which corresponds approximately to the diameter of the target tissue region. Examples of catheters with inflatable energy emitting elements are disclosed in U.S. Pat. No. 5,961,513. The inflatable elements are typically carried by a catheter and are deployed in a collapsed (or folded) and deflated state by way of a sheath whose distal end has been previously positioned near the target tissue region. After passing through the distal end of the sheath, the energy emitting elements are inflated and urged into contact with the target tissue. Energy is then transmitted to the tissue to form a lesion. Inflatable energy emitting elements are advantageous because their pliability facilitates superior tissue contact, which increases the likelihood that continuous lesions will be formed.

The present inventor has determined that conventional inflatable energy emitting elements are susceptible to improvement. For example, conventional inflatable elements occlude blood flow through the vein during use. Another issue identified by the present inventor is related to the fact that the circumference of a lesion formed by a conventional inflatable energy emitting element is dictated by the inflated circumference of the inflatable element. The formation of a lesion with a relatively large circumference requires an energy emitting element with a relatively large inflated circumference, which will also have a relatively large deflated circumference due to the amount of material required to produce the large inflated circumference. However, because inflatable energy emitting elements are advanced though sheaths, the deflated circumference must be smaller than the sheath lumens. The deflated circumference of a conventional energy emitting element is, therefore, the dimension that ultimately dictates the maximum lesion circumference. Similarly, conventional inflatable elements also often require the use of sheaths which are larger than would be otherwise desirable in order to accommodate a deflated inflatable element that will ultimately be inflated to the desired size.

SUMMARY OF THE INVENTION

A probe in accordance with one embodiment of a present invention includes an inflatable therapeutic element that is movable between a coiled state and an uncoiled state. Such a probe provides a number of advantages over conventional probes. For example, the coiled therapeutic element can be brought into contact with the tissue in or around a pulmonary vein or other bodily orifice in such a manner that it defines an opening through which blood or other bodily fluids can pass. Because it is inflatable, it will also be able to provide superior tissue contact.

Another advantage lies in the fact that an inflatable therapeutic element with a relatively small deflated (and inflated) circumference may, when coiled, be used to form a lesion with a relatively large circumference. This is because the lesion circumference will be primarily dictated by the circumference of the coil formed by the inflatable element, not the circumference of the inflated therapeutic element that is to be wound into the coil. As such, a probe that will pass through a sheath with a relatively small lumen may be used to form a lesion with a relatively large circumference.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 1 is a side view of a probe in accordance with a preferred embodiment of a present invention.

FIG. 2 is a side, cutaway view of the distal portion of the probe illustrated in FIG. 1 with the inflatable energy emitting element in a straightened and inflated state.

FIG. 3 is a section view taken along line 3—3 in FIG. 2.

FIG. 4 is a section view taken along line 4—4 in FIG. 2.

FIG. 5 is a section view taken along line 5—5 in FIG. 2.

FIG. 6A is a side, partial section view showing the distal portion of the probe illustrated in FIG. 1 being advanced through a sheath in a straightened and deflated state.

FIG. 6B is a side view showing the distal portion of the probe illustrated in FIG. 1 in a relaxed and inflated state.

FIG. 6C is a side view showing the distal portion of the probe illustrated in FIG. 1 in a longitudinally compressed and inflated state.

FIG. 6D is an end view showing the distal portion of the probe illustrated in FIG. 1 in a longitudinally compressed and inflated state.

FIG. 7 is a side view of a probe in accordance with a preferred embodiment of a present invention in a relaxed and inflated state.

FIG. 8 is an end view of the probe illustrated in FIG. 7.

FIG. 9 is a side, partial section view showing the distal portion of the probe illustrated in FIG. 7 being advanced through a sheath in a straightened and deflated state.

DETAILED DESCRIPTION OF THE PREFERRED EMBODIMENTS

Figure 10:
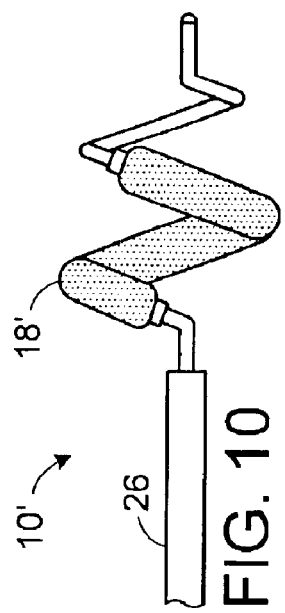
FIG. 10 is a side view of a probe in accordance with a preferred embodiment of a present invention in a relaxed and inflated state.

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:

I. Introduction
II. Exemplary Probe Structures
III. Exemplary Inflatable Elements The section titles and overall organization of the present detailed description are for the purpose of convenience only and are not intended to limit the present inventions.

I. Introduction

The present inventions may be used and performed within body lumens, chambers or cavities for diagnostic or therapeutic purposes in those instances where access to interior bodily regions is obtained through, for example, the vascular system or alimentary canal and without complex invasive surgical procedures. For example, the inventions herein have application in the treatment of arrhythmia conditions within the heart. The inventions herein also have application in the treatment of ailments of the gastrointestinal tract, prostrate, brain, gall bladder, uterus, and other regions of the body. With regard to the treatment of conditions within the heart, the present inventions are designed to produce intimate tissue contact with target substrates within or around the pulmonary vein to, for example, treat ectopic atrial fibrillation.

The inventions may also be embodied in probes other than catheter-based probes such as, for example, hand held surgical devices (or "surgical probes") which incorporate the disclosed helical and loop shaped inflatable energy emitting elements. The distal end of a surgical probe may be placed directly in contact with the targeted tissue area by a physician during a surgical procedure, such as open heart surgery. Here, access may be obtained by way of a thoracotomy, median sternotomy, or thoracostomy. Exemplary surgical probes on which such helical and loop shaped inflatable energy emitting elements may be mounted are disclosed in U.S. Pat. No. 6,142,994, which is incorporated herein by reference.

II. Exemplary Probe Structures

As illustrated FIGS. 1–5, an exemplary catheter 10 in accordance with one embodiment of a present invention includes a hollow, flexible catheter body 12 that is formed from two tubular parts, or members. The proximal member 14 is relatively long and is attached to a handle 20, while the distal member 16, which is relatively short, carries an inflatable energy emitting element 18 (also referred to as the "inflatable element" or "inflatable therapeutic element"). Specific details concerning the exemplary inflatable element 18 are provided in Section III below. The proximal member 14 is typically formed from a biocompatible thermoplastic material, such as a Pebax® material (polyether block emide) and stainless steel braid composite, which has good torque transmission properties. The distal member 16 is typically formed from a softer, more flexible biocompatible thermoplastic material such as unbraided Pebax® material, polyethylene, or polyurethane. The proximal and distal members, which are about 5 French to about 9 French in diameter, are preferably either bonded together with an overlapping thermal bond or adhesively bonded together end to end over a sleeve in what is referred to as a "butt bond." The handle 20 preferably includes a strain relief element 22.

At least a portion of the distal member 16 has a generally helical shape which defines a longitudinal axis that, in the exemplary embodiment, is coincident with the longitudinal axis X—X of the catheter body 12. The number of revolutions (or "coils"), length, diameter, orientation and shape of the helical portion will vary from application to application. The helical portion of the distal member 16 in the embodiment illustrated in FIGS. 1–5 revolves around the longitudinal axis of the catheter body 12 two times. The helical portion also has a generally frusto-conical shape where the diameter decreases in the distal direction. The diameter may, alternatively, be substantially constant over the length of the helical portion.

The inflatable therapeutic element 18 is carried by the helical portion of the distal member 16, thereby creating a helical inflatable energy emitting element. In the exemplary embodiment, the inflatable element 18 extends for at least one revolution, and preferably slightly more than one revolution (e.g. 1¼ revolution), along the helical portion of the distal member 16, and around an inflatable element axis. The inflatable element axis is coaxial with the longitudinal axis X—X of the catheter body 12 in the exemplary embodiment. Catheters in accordance with the present inventions may also be configured such that the inflatable element axis is not coaxial with the longitudinal axis X—X.

When the distal member 16 is longitudinally compressed in the manner described below with reference to FIGS. 6C and 6D, inflatable element 18 will form a generally annular (or "closed loop") structure capable of creating a continuous therapeutic lesion around a pulmonary vein or other bodily orifice. The helical portion of the distal member 16 and the inflatable element 18 also define an open area interior to the inflatable element through which blood or other bodily fluids can flow. As a result, the inflatable element 18 can be used to create a circumferential lesion in or around the pulmonary vein, or other bodily orifice, without occluding fluid flow.

An embodiment configured for use with the pulmonary veins will preferably have a proximal coil outer diameter that will cause the proximal portion to either abut the pulmonary vein ostium or to abut the tissue that is just radially outward of the ostium (i.e. between about 15 mm and about 35 mm), and a distal coil outer diameter suitable for placement within the pulmonary vein (i.e. between about 5 mm and about 10 mm). The catheter 10 will, therefore, be self-centering when inserted into the pulmonary vein because the tapered helical portion will wedge itself against the pulmonary vein ostium and the internal wall of pulmonary vein itself. Not only does this result in proper positioning of the inflatable energy emitting element 18, the wedging effect also prevents beating related movement of the heart from knocking the catheter 10 out of position once it is in place.

An anchor member 24 allows the exemplary catheter 10 to be precisely located relative to the pulmonary vein (or other orifice) during certain methods of use. For example, the anchor member 24 is useful in those instances where the helical portion is deployed within the left atrium and then advanced into contact with the pulmonary vein. In those instances where the helical portion is deployed within the pulmonary vein, the anchor member 24 will stabilize the catheter during deployment and prevent undesirable movement of the helical portion at it exits the sheath 26 (FIG. 6B). The anchor member 24 also helps maintain position after the helical portion has been deployed. The exemplary anchor member 24 is approximately 1 to 2 inches in length. Other lengths may be used, or the anchor member 24 may be eliminated altogether, to suit particular applications.

The exemplary catheter 10 illustrated in FIGS. 1–5 is not a steerable catheter and, accordingly, may be advanced though a conventional guide sheath, such as the sheath 26 illustrated in FIGS. 6A–6D, to the target location. The sheath 26, which should be lubricious to reduce friction during movement of the catheter body 12, may be advanced into position over a guidewire or steerable catheter in conventional fashion. Alternatively, a steerable sheath may be provided. With respect to materials, the proximal portion of the sheath 26 is preferably a Pebax® and stainless steel braid composite and the distal portion is a more flexible material, such as unbraided Pebax®, for steering purposes. The sheath 26 should also be stiffer than the catheter body 12 and may be provided with a soft tip 28, to prevent tissue damage, and/or a radiopaque tip marker 30, to facilitate proper positioning of the distal end of the sheath within the patient. A sheath introducer, such as those used in combination with basket catheters, may be used when introducing the distal member 16 into the sheath 26.

The helical shape of the exemplary distal member 16 may be achieved through the use of a center support 32 (FIG. 3) that is positioned within the catheter body 12 and, more specifically, within a support member lumen 33. The proximal end of the center support 32 is secured to the handle 20, while the distal end is secured to a tip member 34, which is in turn secured to the distal end of the distal member 16 with adhesive. The center support 32 is preferably formed from resilient inert wire, such as Nickel Titanium (commercially available under the trade name Nitinol®) or 17-7 stainless steel wire, with a portion thereof heat set into the desired helical configuration. The helical portion of the distal member 16, the inflatable element 18, and center support 32 should be flexible enough that the helical portion will deflect and straighten out when pushed or pulled into the sheath, yet resilient enough that it will return to its helical shape when removed from the sheath. The center support 32 may be housed in an insulative tube (not shown) formed from material such as Teflon™ or polyester in those instances where the conductor wires (discussed in Section III below) are in the same lumen as the center support. The proximal and distal ends of the helical portion of the catheter 10 should be oriented at an angle relative to the longitudinal axis X—X of the catheter (preferably between about 30 and about 60 degrees and most preferably about 45 degrees) that facilitates a smooth transition as the distal member 16 is pushed or pulled into the sheath 26.

The center support 32 may, alternatively, be formed from material such as actuator-type Nitinol® which has shape memory properties that are activated at a temperature higher than body temperature. The shape memory properties allow the physician to, for example, cause the inflatable element 18 to recoil from the state illustrated in FIG. 6A to the coiled state illustrated in FIG. 6B by energizing the electrodes 44 (FIG. 2). The amount of heat generated by the electrodes 44 during the recoiling should, however, be less than that required to coagulate tissue and form a lesion.

The helical portion of the exemplary catheter 10 illustrated in FIGS. 1–5 is also configured such that its distal region 36 is relatively flexible and its proximal region 38 is relatively stiff. As a result, there is a non-linear force distribution through the coils. The differences in stiffness allows the exemplary catheter 10 to accomplish a number of normally competing goals. In those instances where the helical portion is expanded within the left atrium such that it must then be advanced into contact with a pulmonary vein after it recoils, the physician must often poke around within the atrium as attempts are made to insert the helical structure into the pulmonary vein. The more flexible distal region will, of course, be less likely to traumatize tissue during this process. It is also important that the helical portion be predisposed to easily uncoil for placement within the sheath 26, remain uncoiled and slide though the sheath until it exits through the distal end of the sheath and re-coils, and then easily uncoil again when pulled back into the sheath after the procedure is completed. The stiffer the coils are, the more likely they are to resist uncoiling, which makes it more difficult to get the helical structure into the sheath, and to re-coil within the sheath, which creates friction and makes it more difficult to slide the helical structure through the sheath. Thus, the more flexible distal region 36 will also improve these aspects of the procedure. Good tissue/electrode contact is another important goal in any lesion creation procedure. The stiffer proximal region 38 causes the inflatable energy emitting element 18 to press against the tissue with more force when lesions are being created.

As disclosed in U.S. Patent Application Publication No. US 2001/0020174 A1, which is entitled "Helical And Pre-Oriented Loop Structures For Supporting Diagnostic And Therapeutic Elements In Contact With Body Tissue" and incorporated herein by reference, there are a variety of ways to increase the flexibility of the distal region of helical portion. The configuration of the center support (or "core wire") may, for example, be used to create the desired variations in flexibility. More specifically, the cross-sectional area of the center support will be constant from the handle to proximal end of the helical portion, then taper down along all or part of the helical portion, and then remain constant from the end of the taper to the tip member.

One exemplary method of deploying the exemplary catheter 10 is illustrated in FIGS. 6A–6D. Here, the distal section 16 and inflatable energy emitting element 18 are shown being deployed within the left atrium. Referring first to FIG. 6A, the distal end of the sheath 26 may be directed into the left atrium by, for example, a transseptal procedure and then aligned with the target pulmonary vein. The catheter body 12 is advanced through the sheath 26 with distal section 16 and inflatable element 18 in a straightened (or "uncoiled") state and the inflatable element deflated. The inflatable element 18 is aligned with the longitudinal axis X—X of the catheter body 12, and the distance between the proximal and distal longitudinal ends 18a and 18b of the inflatable element 18 is at its maximum, when the inflatable element is in the straightened state. After the distal section 16 exits the distal end of the sheath 26, the inflatable element 18 will return to the relaxed (or "coiled") state and the inflatable element may be inflated. As illustrated for example in FIG. 6B, the inflatable element 18 will extend around the longitudinal axis X—X and the distance between the longitudinal ends 18a and 18b will be reduced.

Turning to FIGS. 6C and 6D, the catheter 10 may then be urged distally, thereby compressing the helical portion of the distal section 16 and the inflatable energy emitting element 18 against the pulmonary vein ostium or, if desired, the area around the ostium. The proximal and distal longitudinal ends 18a and 18b of the inflatable element 18 will also be adjacent to one another, or at least be generally in the same plane if the inflatable element extends significantly beyond one revolution. As such, the inflatable element 18 will define a generally annular (or "closed loop") structure that is capable of forming a generally annular lesion around the pulmonary vein.

The method described above may be modified slightly. More specifically, in the modified version, the distal portion of the sheath 26 will be steered into the target pulmonary vein. The catheter body 12 will then be directed through the sheath 26 until the distal region 16 is aligned with the portion of the sheath in the vein. The sheath 26 will then be withdrawn, while the position of the catheter body distal portion 16 is maintained within the pulmonary vein. The helical portion of the catheter 10 will return to its coiled state because it is no longer being constrained by the sheath 26 and deploy into the funnel-shaped ostium of the pulmonary vein.

The present inventions are not limited to probes with helically shaped distal regions and inflatable elements. The exemplary catheter 110 illustrated in FIGS. 7–9 is substantially similar to the catheter 10 illustrated in FIGS. 1–6D and similar elements are represented by similar reference numerals. Here, however, the exemplary probe 110 includes a distal section 116 and inflatable energy emitting element 118 that have a generally annular (or "loop-like") shape in the relaxed (or "coiled") state. The energy emitting element 118 extends around an axis that, in the exemplary embodiment, is coincident with the longitudinal axis X—X of the catheter body 112, although this is not required.

The exemplary catheter 110 may be deployed through a sheath 26 in the manner described above with reference to FIGS. 6A–6D. More specifically, the catheter 110 may be advanced through the sheath 26 with distal section 116 and inflatable element 118 in a straightened (or "uncoiled") state and the inflatable element deflated, as is illustrated for example in FIG. 9. The inflatable element 118 is aligned with the longitudinal axis X—X of the catheter body 112 and the distance between the proximal and distal longitudinal ends 118a and 118b of the inflatable element 118 is at its maximum. When the distal section 116 and inflatable element 118 return to the relaxed state illustrated in FIGS. 7 and 8, the inflatable element will extend around the longitudinal axis X—X and the longitudinal ends 118a and 118b will be substantially aligned. The inflatable element 118 may then be inflated and advanced into tissue.

III. Exemplary Inflatable Elements

As illustrated for example in FIGS. 1, 2, 4 and 5, the exemplary inflatable energy emitting element 18 is formed from an electrically non-conductive and conductive thermoplastic or thermosetting plastic material and includes a forward facing conductive region 40 and a non-conductive region 42. Fluid pressure is used to inflate the inflatable element 18 and maintain it in its expanded state in the manner described below. Referring more specifically to FIG. 2, one or more electrodes 44 are carried by the catheter body 12 within the exemplary inflatable energy emitting element 18.

The fluid used to fill the inflatable element 18 is an electrically conductive fluid that establishes an electrically conductive path to convey RF energy from the electrodes 44 to the conductive region 40, and then to the tissue. Although other shapes (such as oval, triangular and rectangular) and sizes may be employed, the exemplary inflatable energy emitting element 18 is substantially circular in cross section has a diameter between about 2.25 mm to about 5 mm when inflated. A preferred inflated diameter is about 3.25 mm. The conductive region 40 and non-conductive region 42 each occupy about 50% of the surface area of the exemplary inflatable element 18, although this ratio may vary based on the intended application. The length of the inflatable element (measured along the longitudinal axis X—X when the inflatable element is straightened) will depend on the circumference of the target tissue region. If a target tissue region has a diameter of about 15 mm and the inflatable element extended for 1¼ revolutions, for example, the length would be equal to about 59 mm based on the formula: length=2Πr+¼(2Πr). Of course, other inflatable element configurations may be employed as applications dictate.

The electrodes 44 should be formed from material with both relatively high electrical conductivity and relatively high thermal conductivity. Suitable materials for the electrodes 44, the length of which preferably ranges from about 1 mm to 6 mm, include gold, platinum, and platinum/iridium. Noble metals are preferred. The conductive region 40 establishes ionic transport of the tissue coagulating energy from the electrodes 44 through the electrically conductive fluid to tissue outside the inflatable element 18.

The electrically conductive fluid which is supplied to the interior region 46 of the inflatable energy emitting element 18 preferably possesses a low resistivity to decrease ohmic loses and thus ohmic heating effects within the inflatable element. The composition of the electrically conductive fluid can vary. A hypertonic saline solution, having a sodium chloride concentration of about 5% is preferred. Hypertonic saline solution has a low resistivity of only about 5 ohm-cm, compared to blood resistivity of about 150 ohm-cm and myocardial tissue resistivity of about 500 ohm-cm. Alternatively, the fluid can be a hypertonic potassium chloride solution. The hypertonic saline solution may also be doped with contrast, such as Diatrizoate Meglumine and Diatrizoate Sodium injection solution, for improved visualization of the inflatable element 18.

Due largely to mass concentration differentials across the conductive region 40, ions in the conductive fluid will pass into the conductive material because of concentration differential-driven diffusion. Ion diffusion through the conductive material will continue as long as a concentration gradient is maintained across the inflatable element 18. The ions contained in the conductive material provide the means to conduct current across the inflatable element 18. When RF energy is conveyed from a RF power supply and control apparatus to the electrodes 44, electric current is carried by the ions within the conductive material. The RF currents provided by the ions result in no net diffusion of ions, as would occur if a DC voltage were applied, although the ions do move slightly back and forth during the RF frequency application. This ionic movement (and current flow) in response to the applied RF field does not require perfusion of fluid through the conductive material. The ions convey RF energy through the conductive material into tissue to a return electrode, which is typically an external patch electrode (forming a unipolar arrangement). Alternatively, the transmitted energy can pass through tissue to an adjacent electrode (forming a bipolar arrangement). The RF energy heats tissue (mostly ohmically) to coagulate the tissue and form a lesion.

The temperature of the fluid is preferably monitored for power control purposes. To that end, one or more thermistors 48 (FIG. 2) may be mounted within the exemplary inflatable element 18. Other temperature sensing devices, such as a thermocouple and reference thermocouple arrangement, may be employed in place of or in addition to the thermistor (s). As illustrated for example in FIGS. 1–5, the electrodes 44 and thermistor 48 are respectively connected to an electrical connector 50 that is associated the handle 20 by conductor wires which extend through a conductor lumen 52 in the catheter body 12. The connector 50 may be connected to a suitable RF power supply and control apparatus. The exemplary probe 10 may operate using a relatively simple control scheme wherein lesions are formed by supplying power to the electrodes 44 at a predetermined level for a predetermined period of time. When forming pulmonary vein lesions, for example, about 35 watts for a period of about 120 seconds is preferred. Should the temperature within the inflatable energy emitting element 18 exceed 90° C., power will be cut off by the control apparatus.

As illustrated for example in FIG. 2, the inflatable element 18 is molded such that the inner diameters of its proximal and distal longitudinal ends 18a and 18b closely correspond to the outer diameter of the catheter body 12. Cyanoacrylate or another suitable adhesive material may be used to secure the proximal and distal ends 18a and 18b in place. Fluid tight seals 54 may also be provided.

With respect to materials, the conductive region 40 is preferably formed from regenerated cellulose or a conductive elastic polymer such as Ticophilic®. Such materials are permeable to mass transfer, but do not permit any significant transfer of fluid. Hydro-Fluoro M material is another exemplary material. Materials such as nylons (with a softening temperature above 100° C.), PTFE, PEI and PEEK that have micropores created through the use of lasers, electrostatic discharge, ion beam bombardment or other processes may also be used. Such materials would preferably include a hydrophilic coating. The micropores should be about 1 to 5 μm in diameter and occupy about 1% of the surface area of the conductive region 40. A slightly larger pore diameter may also be employed. Because the larger pore diameter would result in significant fluid transfer through the porous region, a saline solution having a sodium chloride concentration of about 0.9% weight by volume is preferred. The non-conductive region 42 is preferably formed from relatively elastic materials such as Tecoflex®, silicone, polyisoprene, or UV conformal coating. However, other less elastic materials, such as Nylon®, Pebax®, polyethylene, polyesterurethane and polyester, may also be used. The inflatable energy emitting element 18 may also be provided with creased regions that facilitate collapse. Additional information and examples of inflatable elements are disclosed in U.S. patent application Ser. No. 08/984,414, entitled "Devices and Methods for Creating Lesions in Endocardial and Surrounding Tissue to Isolate Arrhythmia Substrates," U.S. Pat. No. 5,368,591, and U.S. Pat. No. 5,961,513, each of which is incorporated herein by reference.

The inflatable element 18 will typically be filled with conductive fluid after the after the distal section 16 has exited the sheath 26. As illustrated for example in FIGS. 1–5, the conductive fluid is supplied under pressure to the inflatable energy emitting element 18 by way of an infusion lumen 56 and exits the by way of a ventilation lumen 58. The infusion and ventilation lumens 56 and 58 extend from openings 60 and 62 in the distal region of the catheter body 12 to a pair of connectors 64 and 66 in the handle 20. The connectors 64 and 66 may be connected to the infusion and ventilation lines of a fluid supply device (not shown) such as, for example, an infusion pump capable of variable flow rates. Thus, in addition to inflating the inflatable element 18 and providing a conductive path from the electrodes 44 to the tissue, the fluid may be used to cool the inflatable element so that heat is only generated within the tissue by virtue of the passage of current therethrough.

In alternative implementations, the conductive fluid may be supplied to and ventilated from the inflatable element 18 by a single lumen. Here, the inflatable element will simply be inflated and deflated as necessary.

The pressure of the fluid supplied to the inflatable element 18 should be relatively low (less than 5 psi) and may be varied by the fluid supply device in accordance with the desired level of inflation, strength of materials used and the desired degree of flexibility. The pressure is varied manually by the physician. Pressure within the inflatable element 18 may be monitored in a variety of ways. For example, the infusion and ventilation lumens 56 and 58 pressure may be measured by a pressure sensor associated with the fluid supply device. Alternatively, a pressure sensor lumen (not shown) that is filled with non-flowing fluid and extends from the interior of the inflatable element 18 to the pressure sensor associated with the fluid supply device may be used.

Varying the level of pressure within the inflatable element 18 allows the physician to achieve the appropriate level of tissue contact and inflatable element diameter, even when the inflatable element is not perfectly positioned. For example, a stiffer inflatable element 18 (which distorts the tissue) would be preferred when the pulmonary vein ostium is relatively circular and when the ostium tissue is relatively healthy and pliable. A more flexible inflatable element 18 (which conforms to the tissue) would be preferred when the ostium is not circular and the ostium tissue is relatively calcified and rigid due to disease.

Figure 11:
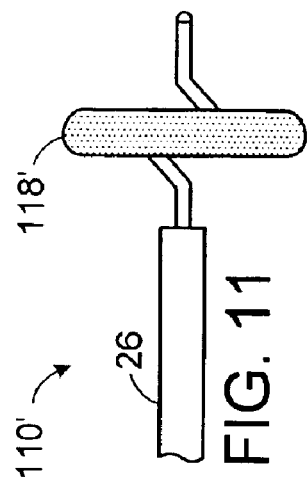
FIG. 11 is a side view of a probe in accordance with a preferred embodiment of a present invention in a relaxed and inflated state.

The present inventions are not limited to the mass transfer permeable or porous region/non-porous region arrangement described above. As illustrated for example in FIGS. 10 and 11, catheters 10' and 110' (which are otherwise identical to catheters 10 and 110) are respectively provided with inflatable energy emitting elements 18' and 118' that do not include non-conductive regions.

Figure 12:
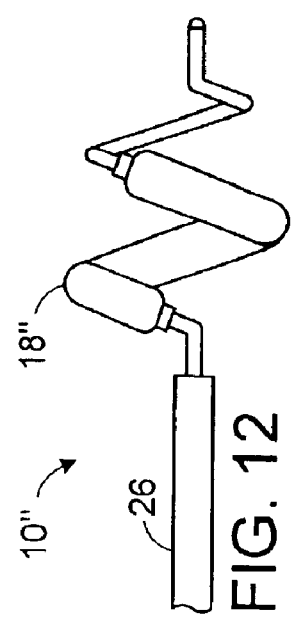
FIG. 12 is a side view of a probe in accordance with a preferred embodiment of a present invention in a relaxed and inflated state.
Figure 14:
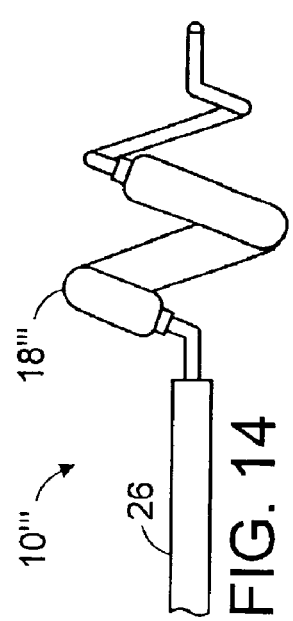
FIG. 14 is a side view of a probe in accordance with a preferred embodiment of a present invention in a relaxed and inflated state.
Figure 13:
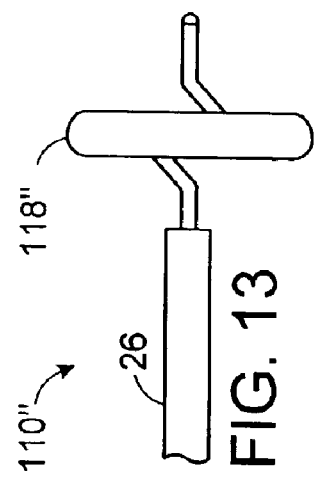
FIG. 13 is a side view of a probe in accordance with a preferred embodiment of a present invention in a relaxed and inflated state.
Figure 15:
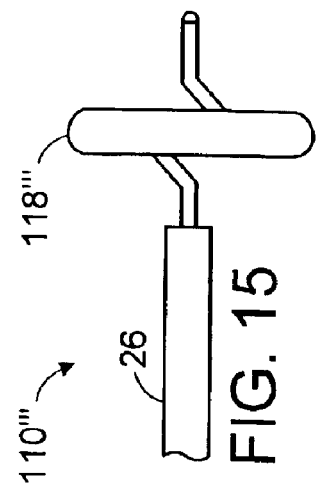
FIG. 15 is a side view of a probe in accordance with a preferred embodiment of a present invention in a relaxed and inflated state.

The present inventions are also not limited to energy emitting inflatable therapeutic elements. Other types of inflatable therapeutic elements may be configured to coil and uncoil in the manner described above. For example, the catheters 10" and 110" illustrated in FIGS. 12 and 13 are substantially similar to the catheters 10 and 110, but for the fact that they include inflatable cryogenic elements 18" and 118". The catheters 10'" and 110'" illustrated in FIGS. 14 and 15 are substantially similar to the catheters 10 and 110, but for the fact that they include inflatable heating elements 18'" and 118'" with an internal fluid heating element. The fluid heating element is preferably one or more electrodes that may be formed from metals such as platinum, gold and stainless steel and mounted on the catheter body. A bi-polar pair of electrodes may, alternatively, be used to transmit power through a conductive fluid, such as isotonic saline solution, to generate heat.

Although the present inventions have been described in terms of the preferred embodiments above, numerous modifications and/or additions to the above-described preferred embodiments would be readily apparent to one skilled in the art. It is intended that the scope of the present inventions extend to all such modifications and/or additions and that the scope of the present inventions is limited solely by the claims set forth below.

I claim:

1. A probe, comprising:
a probe body defining a distal region and a proximal region; and
an inflatable therapeutic element carried by the distal region of the probe body, movable between a coiled state and an uncoiled state, and including a conductive region formed from a porous material that does not permit significant transfer of fluid therethrough.

2. A probe as claimed in claim 1, wherein the probe body comprises a catheter body.

3. A probe as claimed in claim 1, wherein the inflatable therapeutic element defines a substantially helical shape when in the coiled state.

4. A probe as claimed in claim 3, wherein the inflatable therapeutic element defines at least one revolution when in the coiled state.

5. A probe as claimed in claim 1, wherein the inflatable therapeutic element defines a substantially circular shape when in the coiled state.

6. A probe as claimed in claim 5, wherein the inflatable therapeutic element defines at least one revolution when in the coiled state.

7. A probe as claimed in claim 1, wherein inflatable therapeutic element is biased to the coiled state.

8. A probe as claimed in claim 1, wherein the porous material comprises pores that are about 1 $\mu$m to 5 $\mu$m in diameter.

9. A probe as claimed in claim 1, wherein the inflatable therapeutic element includes a non-conductive region.

10. A probe, comprising:
a probe body defining a distal region, a proximal region and a probe body axis; and
an inflatable therapeutic element carried by the probe body and defining proximal and distal longitudinal ends, the inflatable therapeutic element being movable between a coiled state wherein the inflatable therapeutic element extends around a therapeutic element axis to define an open region and at least the proximal longitudinal end is substantially spaced from the therapeutic element axis, and an uncoiled state wherein the longitudinal ends of the inflatable therapeutic element are substantially aligned with the therapeutic element axis.

11. A probe as claimed in claim 10, wherein the probe body comprises a catheter body.

12. A probe as claimed in claim 10, wherein the inflatable therapeutic element comprises a conductive inflatable therapeutic element.

13. A probe as claimed in claim 10, wherein the inflatable therapeutic element comprises an energy emitting inflatable therapeutic element.

14. A probe as claimed in claim 10, wherein the inflatable therapeutic element defines a substantially helical shape when in the coiled state.

15. A probe as claimed in claim 14, wherein the inflatable therapeutic element defines at least one revolution when in the coiled state.

16. A probe as claimed in claim 10, wherein the inflatable therapeutic element defines a substantially circular shape when in the coiled state.

17. A probe as claimed in claim 16, wherein the inflatable therapeutic element defines at least one revolution when in the coiled state.

18. A probe as claimed in claim 10, wherein inflatable therapeutic element is biased to the coiled state.

19. A probe as claimed in claim 10, wherein the distal end of the inflatable therapeutic element is also substantially spaced from the therapeutic element axis when the inflatable therapeutic element is in the coiled state.

20. A method of performing tissue therapy with a probe including an inflatable therapeutic element, the method comprising the steps of:

advancing the probe to a target tissue region;

coiling the inflatable therapeutic element;

inflating the inflatable therapeutic element with an electrically conductive fluid; and performing a therapeutic operation with the inflatable therapeutic element coiled and inflated.

21. A method as claimed in claim 20, wherein the step of advancing the probe comprises advancing the probe to a target tissue region with the inflatable therapeutic element in an uncoiled state.

22. A method as claimed in claim 20, wherein the step of coiling the inflatable therapeutic element comprises coiling the inflatable therapeutic element into a substantially helical shape.

23. A method as claimed in claim 20, wherein the step of coiling the inflatable therapeutic element comprises coiling the inflatable therapeutic element into a substantially circular shape.

24. A method of performing tissue therapy with a probe including an inflatable therapeutic element, the method comprising the steps of:

advancing the probe to a target tissue region;

coiling the inflatable therapeutic element;

inflating the inflatable therapeutic element; and forming a lesion with the inflatable therapeutic element coiled and inflated.

25. A method as claimed in claim 24, wherein the step of forming a lesion with the inflatable therapeutic element coiled and inflated comprises forming a lesion by transmitting energy to tissue with the inflatable therapeutic element coiled and inflated.

26. A method as claimed in claim 24, wherein the step of advancing the probe comprises advancing the probe to a target tissue region with the inflatable therapeutic element in an uncoiled state.

27. A method as claimed in claim 24, wherein the step of coiling the inflatable therapeutic element comprises coiling the inflatable therapeutic element into a substantially helical shape.

28. A method as claimed in claim 24, wherein the step of coiling the inflatable therapeutic element comprises coiling the inflatable therapeutic element into a substantially circular shape.

29. A probe, comprising:

a probe body; and an inflatable therapeutic element carried by the probe body and defining proximal and distal longitudinal ends, the inflatable therapeutic element being movable between a relaxed state wherein the inflatable therapeutic element extends around a therapeutic element axis and the longitudinal ends are substantially aligned with one another, and a substantially straightened state wherein the longitudinal ends of the inflatable therapeutic element are substantially spaced apart and substantially aligned with the therapeutic element axis.

30. A probe as claimed in claim 29, wherein the probe body comprises a catheter body.

31. A probe as claimed in claim 29, wherein the inflatable therapeutic element comprises a conductive inflatable therapeutic element.

32. A probe as claimed in claim 29, wherein the inflatable therapeutic element comprises an energy emitting inflatable therapeutic element.

33. A probe as claimed in claim 29, wherein the inflatable therapeutic element defines a substantially circular shape when in the relaxed state.

34. A probe as claimed in claim 33, wherein the inflatable therapeutic element defines at least one revolution when in the relaxed state.

* * * * *